(12) United States Patent
Muratore et al.

(10) Patent No.: US 11,359,162 B2
(45) Date of Patent: Jun. 14, 2022

(54) SPIROOXATHIOLANONE COMPOUNDS, THEIR PREPARATION METHOD AS WELL AS THEIR USE IN PERFUME-MAKING AND AROMATICS

(71) Applicant: V. MANE FILS, Bar sur Loup (FR)

(72) Inventors: Agnès Muratore, Chateauneuf de Grasse (FR); Fabien Grasset, Grasse (FR)

(73) Assignee: V. MANE FILS, Bar sur Loup (FR)

( * ) Notice: Subject to any disclaimer, the term of this patent is extended or adjusted under 35 U.S.C. 154(b) by 0 days.

(21) Appl. No.: 16/964,874

(22) PCT Filed: Jan. 23, 2019

(86) PCT No.: PCT/EP2019/051597
§ 371 (c)(1),
(2) Date: Jul. 24, 2020

(87) PCT Pub. No.: WO2019/145347
PCT Pub. Date: Aug. 1, 2019

(65) Prior Publication Data
US 2021/0032563 A1  Feb. 4, 2021

(30) Foreign Application Priority Data
Jan. 25, 2018 (FR) ...................... 1850613

(51) Int. Cl.
*C11B 9/00* (2006.01)
*A61K 8/49* (2006.01)
*A61Q 5/02* (2006.01)
*A61Q 13/00* (2006.01)
*C07D 327/04* (2006.01)

(52) U.S. Cl.
CPC .............. *C11B 9/0088* (2013.01); *A61K 8/49* (2013.01); *A61Q 5/02* (2013.01); *A61Q 13/00* (2013.01); *C07D 327/04* (2013.01)

(58) Field of Classification Search
CPC ......... C11B 9/0088; A61Q 13/00; A61Q 5/02; A61K 8/49; C07D 327/04
See application file for complete search history.

(56) References Cited

U.S. PATENT DOCUMENTS 4,519,944 A     5/1985  Dahill et al.
2006/0249167 A1  11/2006  Giersch et al.

FOREIGN PATENT DOCUMENTS

JP    2001039972    2/2001

OTHER PUBLICATIONS

Clive, et al. "A Free Radical Method for Reduction of Cyclohexanones—Preferential Formation of Equatorial Alcohols", Synthetic Communications, vol. 33, No. 11, pp. 1951-1961, 2003. (Year: 2003).*
International Search Report for PCT/EP2019/051597, dated Feb. 14, 2019.
Written Opinion of the International Searching Authority for PCT/EP2019/051597, dated Feb. 14, 2019.

* cited by examiner

*Primary Examiner* — Arrie L Reuther
(74) *Attorney, Agent, or Firm* — B. Aaron Schulman, Esq.; Stites & Harbison, PLLC

(57) ABSTRACT

The present invention concerns new fragrant and aromatic compounds presenting peach, fruity and/or exotic fruit notes, but with no lactonic and fat aspects. More specifically, new spirooxathiolanone-type compounds responding to the following general formula (I) are disclosed:

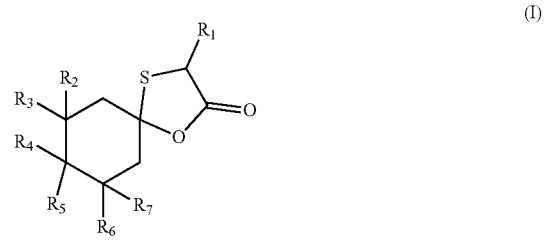

(I)

as well as a method for synthesising said compounds and their uses.

18 Claims, No Drawings

SPIROOXATHIOLANONE COMPOUNDS, THEIR PREPARATION METHOD AS WELL AS THEIR USE IN PERFUME-MAKING AND AROMATICS

The present invention aims for new spirooxathiolanone-type compounds having fruity, peach and/or exotic fruit notes, their preparation method, as well as their uses in the chemical industry, and in particular in perfume-making, cosmetics, para-pharmacy, in the detergents industry, as well as in food, said compounds having useful organoleptic properties, as well as a particular power and persistence.

In order to increase the range of notes available to perfume-makers and flavourists to accompany their creations, the perfume and aromatics industry is perpetually searching for new organoleptic compounds, both meeting increasing regulatory requirements, but also in view of replacing the compounds identified by the legislator as undesirable, even unacceptable. Also, cost constraints are greater and greater.

From among organoleptic molecules, the compounds provided with fruity, peach and/or exotic fruit notes are very few. From among the compounds most used, there are gamma-undecalactone, Nectaryl® (Givaudan) or Apritone® (Bedoukian):

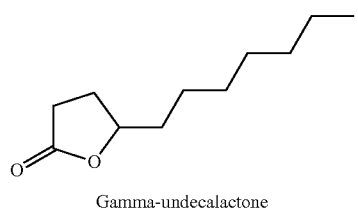

Gamma-undecalactone

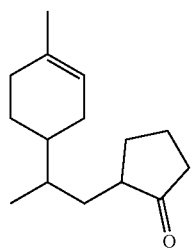

Nectaryl ®

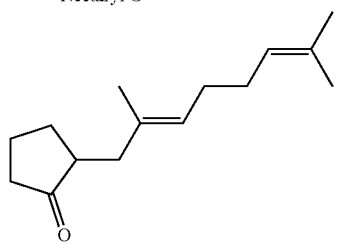

Apritone ®

However, the compounds of the prior art and in particular those above have fruity and/or exotic fruit notes always accompanied by a fatty, lactone, creamy side, which gives a non-natural aspect to the aroma or to the perfume, which is not advantageous.

Also, in order to cope with the constant needs of the perfume and aromatics industry, and to expand the palette for perfume-makers and flavourists, the Applicant has identified new spirooxathiolanone compounds presenting an original fruity, peach and/or exotic fruit note, which have the advantage of giving a natural aspect to the compositions. These compounds have sufficiently powerful notes to allow a use with a very low final content in ready-to-use olfactive and gustative compositions.

These spirooxathiolanone compounds respond to the following formula (I):

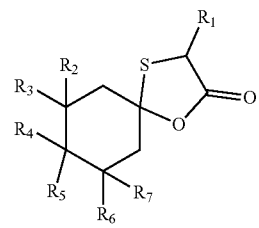

wherein:
$R_1$, $R_2$, $R_3$, $R_4$, $R_6$ and $R_7$, represent independently a hydrogen atom or a methyl group;
$R_5$ represents a hydrogen atom or a saturated linear $C_1$-$C_5$ alkyl group;
$R_4$ and $R_5$ could together form a cyclopentyl group;
the total number of carbon atoms being strictly greater than 9.

The present invention also relates to a composition comprising at least one compound of general formula (I).

Furthermore, a third aim of the present invention relates to a method for preparing a compound of general formula (I), said method being simple, advantageous in terms of yield, comprising one single step and therefore inexpensive.

Finally, a last aim of the present invention relates to the use of at least one compound of general formula (I) to give, modify or reinforce the organoleptic properties of a substance, a composition or an article.

To the knowledge of the Applicant, none of the compounds responding to the general formula (I) has been identified beforehand.

Spirolactone compounds used in perfume-making have been identified in the prior art, like for example, in U.S. Pat. No. 4,519,944 which discloses compounds of following formula:

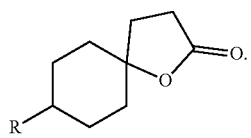

These compounds are not only different structurally from compounds of the present invention, but they present (for the preferred compounds) woody, milky, lactone, powdery notes, notes which are therefore truly different from the compounds described in the present invention.

Moreover, scientific publications disclose certain spirooxathiolanone compounds, but without identifying their organoleptic properties. For example, 7-methyl-1-oxa-4-thiaspiro[4.5]decan-2-one and 3-methyl-1-oxa-4-thiaspiro[4.5]decan-2-one (Tetrahedron, 1970, 26(19), 4641-4648), as well as 8-tert-butyl-1-oxa-4-thiaspiro[4.5]decan-2-one (Synth. Commun., 2003, 33(11), 1951-1961) are cited.

Finally, patent application JP 2001039972 (Hasegawa) describes oxathiolanones having a meaty, nutty, culinary odour, of general formula:

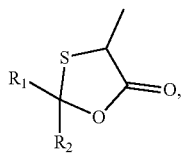

therefore, truly far from the fruity, peach and/or exotic notes of the compounds described in the present invention.

The spirooxathiolane compounds of the present invention have, on the one hand, a chemical structure which is truly distinct and new from that of the compounds of the prior art and, on the other hand, fruity, peach, and/or exotic fruit notes giving a natural aspect to the compositions and with respect to the reference compounds. Moreover, the compounds according to the invention have very low detection thresholds of the odour, in particular compared with the reference compound that is gamma-undecalactone. Still compared with gamma-undecalactone, the spirooxathiolane compounds of the present invention have an "odour value", obtained by the volatility/detection threshold ratio of the odour), a lot more significant than that of gamma-undecalactone, which thus demonstrates the power of said compounds with respect to that of gamma-undecalactone.

Thus, the present invention relates to spirooxathiolanone compounds of following general formula (I):

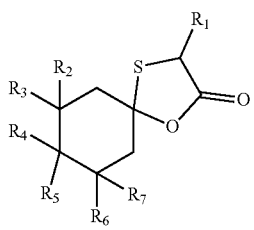

wherein:
$R_1$, $R_2$, $R_3$, $R_4$, $R_6$ and $R_7$, represent independently a hydrogen atom or a methyl group;
$R_5$ represents a hydrogen atom or a saturated linear $C_1$-$C_5$ alkyl group;
$R_4$ and $R_5$ could together form a cyclopentyl group;
the total number of carbon atoms being strictly greater than 9.

In the sense of the present invention, the term "$C_1$-$C_5$ alkyl" means any monovalent radical derived from a saturated linear carbonated chain, containing 1 or 5 carbon atoms, i.e. a methyl, ethyl, propyl, butyl and pentyl group.

According to a first embodiment, $R_5$ represents a saturated linear $C_1$-$C_5$ alkyl group. Preferably, $R_5$ represents a ethyl or propyl group.

According to another preferred embodiment, $R_1$, $R_2$, $R_3$, $R_4$, $R_6$ and $R_7$, represent a hydrogen atom.

More specifically, the total number of carbon atoms is 10 or 11.

According to another preferred embodiment, the total number of carbon atoms is 12.

In a preferred embodiment, the compound according to the present invention is selected from among 7,7-dimethyl-1-oxa-4-thiaspiro[4.5]decan-2-one, 8-ethyl-1-oxa-4-thiaspiro[4.5]decan-2-one, 8-ethyl-3-methyl-1-oxa-4-thiaspiro[4.5]decan-2-one, 8,8-dimethyl-1-oxa-4-thiaspiro[4.5]decan-2-one, 8-propyl-1-oxa-4-thiaspiro[4.5]decan-2-one, 3-methyl-8-propyl-1-oxa-4-thiaspiro[4.5]decan-2-one, spirooxathiolanone[4.5]decan-8-one, 7,7,9-trimethyl-1-oxa-4-thiaspiro[4.5]decan-2-one and 8-pentyl-1-oxa-4-thiaspiro[4.5]decan-2-one.

The presence of asymmetrical centres in the structure of the compounds of formula (I) according to the invention causes the existence, for each of the, of several enantiomeric and/or diastereomeric forms. The invention also covers the compounds represented by the general formula (I) in the form of enantiomeric and/or diastereomeric mixtures, in variable proportions, in particular racemic mixtures. The invention also comprises the compounds of formula (I) in the form of one single enantiomer and/or diastereomer. Enantiomeric/diastereomeric mixtures or pure forms can be obtained by synthesis from starting products, optically enriched or optically pure, or by means of methods of separation by crystallisation or chromatography.

A second aim of the present invention relates to a composition comprising at least one compound of general formula (I)

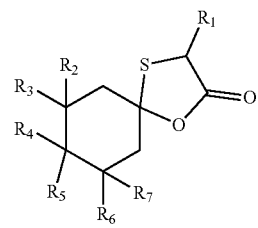

wherein:
$R_1$, $R_2$, $R_3$, $R_4$, $R_6$ and $R_7$, represent independently a hydrogen atom or a methyl group;
$R_5$ represents a hydrogen atom or a saturated linear $C_1$-$C_5$ alkyl group;
$R_4$ and $R_5$ could together form a cyclopentyl group;
the total number of carbon atoms being strictly greater than 9.

Preferably, a composition according to the present invention comprises at least one compound selected from among 7,7-dimethyl-1-oxa-4-thiaspiro[4.5]decan-2-one, 8-ethyl-1-oxa-4-thiaspiro[4.5]decan-2-one, 8-ethyl-3-methyl-1-oxa-4-thiaspiro[4.5]decan-2-one, 8,8-dimethyl-1-oxa-4-thiaspiro[4.5]decan-2-one, 8-propyl-1-oxa-4-thiaspiro[4.5]decan-2-one, 3-methyl-8-propyl-1-oxa-4-thiaspiro[4.5]decan-2-one, spirooxathiolanone[4.5]decan-8-one, 7,7,9-trimethyl-1-oxa-4-thiaspiro[4.5]decan-2-one and 8-pentyl-1-oxa-4-thiaspiro[4.5]decan-2-one.

The effective quantity of the compounds of the invention to be incorporated in these compositions is according to the nature of said compositions, of the odorising or flavouring effect sought and of the nature of the other odorising or flavouring compounds possibly present. It is easily determined by a person skilled in the art, and can vary in a very wide range, from 0.000001 to 50%, in particular 0.000005 to 20%. The preceding percentages are expressed by total weight of the composition.

In a first particular embodiment, the composition according to the invention is a perfume composition comprising at least one compound of general formula (I) and at least one other odorising substance. Other odorising substances which could be used in combination with the compounds of the present invention can be natural products such as extracts, essential oils, absolutes, resinoids, resins, concretes, etc., but also synthesis products such as hydrocarbons, alcohols, aldehydes, ketones, ethers, acids, esters, acetals, nitriles, etc., in particular saturated or unsaturated, aliphatic, heterocyclic or carbocyclic compounds. Such odorising substances are mentioned, for example, in S. Arctander, "Perfume and Flavor Chemicals" (Montclair, N.J., 1969), or also in "Common Fragrance and Flavor Materials", Wiley-VCH, Weinheim, 2006. Finally, several compounds of the present invention can also be used in combination in one same composition.

Due to the pleasant odour that they release, the compounds of the invention have a number of application in perfume-making. The term "perfume-making" is used here in its general sense; it not only designates traditional perfume-making (alcoholic or not), but also other fields wherein the odour of the products is important. Reference can thus be made to perfume-making compositions in the usual and traditional sense (such as perfuming bases and concentrates, perfumes, cologne, eaux de toilette, air fresheners, room fragrances, scented candles and similar products), to topical, in particular cosmetic compositions (such as face and/or body creams, talcum powders, hair oils, shampoos, hair lotions, bath salts and oils, shower and/or bath gels, bath soaps, antiperspirants and body deodorants, shaving lotions and creams, soaps, toothpastes, mouthwashes, balms, and similar products), as well as to maintenance products, in particular household maintenance products (such as detergents, washing detergents, softeners, air fresheners, room fragrances and similar products).

The invention thus extends to a perfume composition comprising at least one compound of the invention. It can, in particular, relate to a traditional perfume-making composition, a cosmetic composition, maintenance product, or also a "so-called intermediate composition", intended to be used for preparing end compositions or end products (in particular, perfumes, cosmetic products, maintenance products).

Such a perfumed composition is generally prepared from a base product, wherein the compound(s) of the invention are incorporated. The base product will be easily determined by a person skilled in the art according to the composition considered and therefore of the use considered. The composition of these base products and the nature of their usual components, such as solvent(s) and/or additive(s), are well-known to a person skilled in the art.

The compounds entering into these perfumed compositions, in particular the compounds of the invention, can be incorporated in or on an inert support material. The support materials which could be used are numerous and varied, for example polar solvents, oils, fats, finally divided solids, cyclodextrins, maltodextrins, gums, resins and any other support material known for such compositions (for example, soaps, candles, balms, textiles, wipes, perfumed gels, etc.).

According to another particular embodiment, the composition according to the invention is an aromatic composition comprising at least one compound of formula (I) and at least one other aromatic substance.

More specifically, the aromatic composition is an ingestible product, which refers to a "foodstuff", an "edible composition" and/or a "food product". The aromatic composition can also be intended to be used in tobacco. Said ingestible product preferably relates to, without being limited to, products intended for human food, intended for animal food (pets) or also for pharmaceutical compositions. Examples of products intended for human food can include, without limiting it, snacks, sweets, vegetable substances and meals which can (or not) provide essential nutrients. The vegetable substances comprise cocoa, cocoa beans, coffee, coffee beans and tealeaves or powder. Non-limiting examples of food products comprises vinaigrettes, sauces, marinades, sticks, nutrition bars, pastries, breads, caramel, cooked cereals, meat products, poultry products, meat, poultry, fish, marine protein sources, beans, pastas, sweets products, salted snacks, dairy products, cheeses, yogurts, butter, margarine, ready-to-eat cereals, condiments and sauces and drinks. In particular, the term "drink" comprises mixtures and concentrates, including, but without limitation, alcoholic and non-alcoholic ready-to-drink drinks and dry powdered drinks. Non-limiting examples of drinks comprise fizzy drinks, brewed drinks, dairy products, drinking yogurt, milk, whitening agents for coffee, nutritional drinks. Non-limiting examples of food intended for animals can include: food for pets, more specifically dogs and cats, food for rodents, food for cattle, food for bovines, food for horses and similar.

A third aim of the present invention relates to a method for preparing compounds of formula (I) such as defined above.

Said method is advantageous in the sense that it is carried out in one single step and allows the use of raw materials available in a large quantity. The yield of said method is also advantageous in that it is very high (almost 80%).

The compounds of the present invention are obtained by a cyclisation reaction between a cycloalkanone of formula (II) and a thiol acid of formula (III) in the presence of an acid:

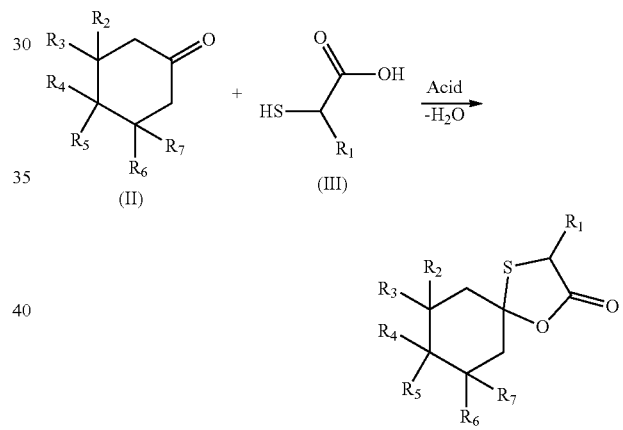

wherein:
$R_1$, $R_2$, $R_3$, $R_4$, $R_6$ and $R_7$, represent independently a hydrogen atom or a methyl group;
$R_5$ represents a hydrogen atom or a saturated linear $C_1$-$C_5$ alkyl group;
$R_4$ and $R_5$ could together form a cyclopentyl group;
the total number of carbon atoms being strictly greater than 9.

In a first embodiment, the thiol acid is thioglycolic acid.
In a second embodiment, thiol acid is thiolactic acid.
Preferably, the acid used is sulphonic para-toluene acid. Even more preferably, between 1 to 5% molar of sulphonic para-toluene acid are used with respect to the reagents. The reaction is in particular conducted at reflux at around 70° C. in cyclohexane.

Finally, the invention lastly aims at the use of at least compound of formula (I) according to the invention in the form of a stereoisomer or a mixture of stereoisomer, or a racemic mixture to give, modify or reinforce the organoleptic properties of a substance, of a composition or of an article.

By "organoleptic properties", this means any property likely to modify, improve or reinforce the organoleptic perception of a substance, of a composition, of an article by a user.

In a first embodiment, at least one compound of formula (I) is used as a fragrant agent, individually or in combination with at least one other odorising substance, and/or at least one solvent, and/or at least one additive. Additional odorising agent(s), solvents and additives are known to a person skilled in the art who will be able to choose the most suitable ones according to the effect sought.

The term "fragrant", is used here to designate any pleasantly scented stimulating organoleptic compound.

The compounds according to the invention can particularly be used as a masking agent or as an odour neutralising agent. By the term "masking agent" or "odour neutralising agent", this means reducing or removing the perception of a bad odour generated by one or more molecules entering into the composition of a product.

In a second embodiment, at least one compound of general formula (I) is used as an aromatic compound, individually or in combination with at least one other aromatic substance and/or at least one solvent, and/or at least one additive.

Additional aromatising agents, solvents and additives are known to a person skilled in the art which will be quite capable of selecting the more suitable ones according to the effect sought. The solvents used, not only an exact dosing of the compound according to the invention for food and drinks, but also facilitates a uniform distribution of the compound according to the invention in food and drinks. Suitable solvents can be hydrophilic solvents like water, glycol propylene, glycerol, ethanol and triacetin or hydrophobic solvents such as vegetable oils, for example palm oil, soybean oil, rapeseed oil, sunflower oil, peanut oil, medium chain triglycerides (MCT). Medium chain triglycerides are aliphatic fatty acid-based triglycerides comprising 6 to 12 carbon atoms.

By aromatic, this means any use of compounds of the invention to aromatise any liquid or solid, human or animal foodstuff, in particular drinks, dairy products, ice creams, but also in applications for flavouring tobacco.

Particularly, the compounds according to the invention can be used individually or in combination with taste-modulating compounds, i.e. which modify the taste and the sensorial perceptions. In any case, the specificity of such taste-modulating compounds is that they have no taste and perceptible aromatic properties (with no taste and with no aroma). Such compounds modifying the aroma can be of synthetic origin or of natural origin.

The following examples illustrate a particular way to prepare the compounds of the invention, as well as the olfactive/aromatic profile of each of the compounds given as examples. These examples are only given with an aim of illustration and must not be comprised as limiting the general scope of the invention.

EXAMPLE 1

Preparation of 7,7-dimethyl-1-oxa-4-thiaspiro[4.5]decan-2-one 3,3-dimethylcyclohexanone (whose preparation is disclosed, for example, in the application WO 2010043522) is placed in 1.1 equivalents of thioglycolic acid and 4 volumes of cyclohexane. At ambient temperature, 0.05 equivalent of sulphonic para-toluene acid is added. The reaction media is brought to reflux while the water formed is removed by azeotropic distillation. When the reaction is ended, the reaction media is poured on an aqueous solution saturated in sodium bicarbonate. The organic phase is washed with water up to neutral pH. After drying on magnesium sulphate, filtration and concentration, the raw product is distilled under reduced pressure: its boiling point is 89° C. under 0.26 torr.

Olfactive Description: Fruity, Peach, Raspberry Effect.

7,7-dimethyl-1-oxa-4-thiaspiro[4.5]decan-2-one thus obtained presents the following spectral features:

$^1$H-RMN (300 MHz, CDCl$_3$): δ (ppm) 3.73 (s, 1H), 3.72 (s, 1H), 2.10-1.90 (m, 2H), 1.85-1.58 (m, 4H), 1.46-1.29 (m, 1H), 1.34-1.16 (m, 1H), 1.04 (s, 3H), 0.97 (s, 3H).

$^{13}$C-RMN (75 MHz, CDCl$_3$): δ (ppm) 172.34, 92.16, 51.31, 39.82, 37.74, 32.23, 31.11, 28.37, 19.90.

SM [EI$^+$] (m/z) (%): 200 (M+, 9), 127 (100), 109 (55), 83 (25), 69 (34), 56 (10), 55 (35), 46 (12), 43 (26), 41 (25), 39 (10).

IR (pure, cm$^{-1}$): 2946m, 1765s, 1455w, 1215m, 1144m, 1060m, 1025m, 993m, 954m, 914w, 811w, 797w, 607w.

EXAMPLE 2

Preparation of 8-ethyl-1-oxa-4-thiaspiro[4.5]decan-2-one 8-ethyl-1-oxa-4-thiaspiro[4.5]decan-2-one is prepared according to the protocol described I example 1 by using 4-ethylcyclohexanone instead of 3,3-dimethylcyclohexanone. The raw product, obtained in the form of two diastereoisomers in proportions 54:46, is distilled under reduced pressure: its boiling point is 98° C. under 0.18 torr.

Olfactive Description: Exotic Fruits, Mango, Guava, Papaya.

8-ethyl-1-oxa-4-thiaspiro[4.5]decan-2-one thus obtained presents the following spectral features:

Major Isomer (54%):

$^1$H-RMN (300 MHz, CDCl$_3$): δ (ppm) 3.62 (s, 2H), 2.21-2.06 (m, 1H), 2.05-1.88 (m, 2H), 1.80-1.60 (m, 3H), 1.40-1.23 (m, 1H), 1.26-1.04 (m, 4H), 0.81 (td, J=7.2 Hz, 3H).

$^{13}$C-RMN (75 MHz, CDCl$_3$): δ (ppm) 172.24, 94.34, 38.70, 37.43, 31.69, 39.34, 11.57.

SM [EI$^+$] (m/z) (%): 200 (M+, 10), 127 (100), 109 (37), 67 (33), 55 (41), 46 (12), 43 (13), 41 (22).

Minor Isomer (46%):

$^1$H-RMN (300 MHz, CDCl$_3$): δ (ppm) 3.69 (s, 2H), 2.21-2.06 (m, 1H), 2.05-1.88 (m, 2H), 1.80-1.60 (m, 3H), 1.40-1.23 (m, 1H), 1.26-1.04 (m, 4H), 0.81 (td, J=7.2 Hz, 3H).

$^{13}$C-RMN (75 MHz, CDCl$_3$): δ (ppm) 172.26, 91.48, 39.49, 37.17, 32.25, 29.12, 28.69, 11.47.

SM [e/m (%)]: 200 (M+, 10), 129 (10), 127 (100), 109 (35), 67 (33), 55 (42), 46 (12), 43 (14), 41 (23).

IR (pure, cm$^{-1}$): 2926m, 1767s, 1442w, 1197m, 1139m, 1041m, 966m, 915w, 892w, 854w, 796w.

EXAMPLE 3

Preparation of 8-ethyl-3-methyl-1-oxa-4-thiaspiro[4.5]decan-2-one 8-ethyl-3-methyl-1-oxa-4-thiaspiro[4.5]decan-2-one is prepared according to the protocol described in example 1 by using 4-ethylcyclohexanone instead of 3,3-dimethylcyclohexanone, thiolactic acid (1.3 equivalents) instead of thioglycolic acid and toluene instead of cyclohexane. The raw product, obtained in the form of two diastereoisomers in proportions 42:58 is distilled under reduced pressure: its boiling point is 88° C. under 0.4 mbar.

Olfactive Description: Peach, Green, Tomato Leaf 8-ethyl-3-methyl-1-oxa-4-thiaspiro[4.5]decan-2-one thus obtained presents the following spectral features:

Major Isomer (58%):

$^1$H-RMN (300 MHz, CDCl$_3$): δ (ppm) 3.99 (q, J=7.0 Hz, 1H), 2.28-2.09 (m, 1H), 2.09-1.61 (m, 5H), 1.57 (d, J=7.0 Hz, 3H), 1.52-0.95 (m, 5H), 0.88 (t, J=7.0 Hz, 3H).

$^{13}$C-RMN (75 MHz, CDCl$_3$): δ (ppm) 175.19, 91.63, 40.90, 39.61, 38.96, 37.52, 29.78, 29.15, 28.71, 18.40, 11.60.

SM [EI$^+$] (m/z) (%): 210 (M+, 0.3), 195 (100), 137 (24), 109 (34), 101 (998), 93 (10), 91 (14), 81 (11), 79 (15), 76 (15), 67 (16), 43 (64), 41 (16).

Minor Isomer (42%):

$^1$H-RMN (300 MHz, CDCl$_3$): δ (ppm) 3.99 (q, J=7.0 Hz, 1H), 2.28-2.09 (m, 1H), 2.09-1.61 (m, 5H), 1.58 (d, J=7.0 Hz, 3H), 1.52-0.95 (m, 5H), 0.87 (t, J=7.0 Hz, 3H).

$^{13}$C-RMN (75 MHz, CDCl$_3$): δ (ppm) 175.25, 88.74, 41.43, 40.27, 39.74, 37.28, 29.23, 29.06, 28.76, 18.54, 11.50.

SM [EI$^+$] (m/z) (%): 214 [M$^+$] (6), 127 (100), 109 (19), 67 (12), 60 (20), 55 (23), 41 (15).

IR (film, cm$^{-1}$): 1039m, 1209m, 1447s, 1761s, 2928m.

EXAMPLE 4

Preparation of 8,8-dimethyl-1-oxa-4-thiaspiro[4.5]decan-2-one 8,8-dimethyl-1-oxa-4-thiaspiro[4.5]decan-2-one is prepared according to the protocol described in example 1 by using 4,4-dimethylcyclohexanone instead of 3,3-dimethylcyclohexanone. The raw product is distilled under reduced pressure: its boiling point is 92° C. under 0.39 torr.

Olfactive Description: Fruity, Green, Exotic Fruits.

8,8-dimethyl-1-oxa-4-thiaspiro[4.5]decan-2-one thus obtained has the following spectral features:

$^1$H-RMN (300 MHz, CDCl$_3$): δ (ppm) 3.71 (s, 2H), 2.19-2.01 (m, 2H), 1.98-1.80 (m, 2H), 1.63-1.30 (m, 4H), 0.94 (2s, 6H).

$^{13}$C-RMN (75 MHz, CDCl$_3$): δ (ppm) 172.35, 93.19, 36.05, 35.74, 31.95, 29.11.

SM [EI$^+$] (m/z) (%): 200 (M+, 12), 127 (100), 109 (35), 71(15), 67 (16), 55 (33), 46 (15), 43 (24), 41 (24), 39 (10).

IR (pure, cm$^{-1}$): 2950m, 1767s, 1444w, 1232m, 1215m, 1156m, 1045s, 1001m, 972m, 877m, 791w, 585w.

EXAMPLE 5

Preparation of 8-propyl-1-oxa-4-thiaspiro[4.5]decan-2-one 8-propyl-1-oxa-4-thiaspiro[4.5]decan-2-one is prepared according to the protocol described in example 1 by using 4-propylcyclohexanone instead of 3,3-dimethylcyclohexanone. The raw product, obtained in the form of two diastereoisomers in proportions 46:54, is distilled under reduced pressure: its boiling point is 106-110° C. under 0.2 torr.

Olfactive Description: Peach, Apricot, Juicy, Pulp.

8-propyl-1-oxa-4-thiaspiro[4.5]decan-2-one thus obtained presents the following spectral features:

Major Isomer (54%):

$^1$H-RMN (300 MHz, CDCl$_3$): δ (ppm) 3.74 (s, 2H), 2.22-2.16 (m, 1H), 2.05-1.95 (m, 2H), 1.85-1.64 (m, 3H), 1.40-1.11 (m, 7H), 0.89-0.84 (t, J=7.2 Hz, 3H).

$^{13}$C-RMN (75 MHz, CDCl$_3$): δ (ppm) 172.38, 94.50, 38.79, 38.27, 31.78, 29.73, 20.12, 14.27.

SM [EI$^+$] (m/z) (%): 214 (M+, 7), 142 (10), 141 (100), 81 (43), 67 (20), 55 (28), 46 (10), 43 (10), 41 (18).

Minor Isomer (46%):

$^1$H-RMN (300 MHz, CDCl$_3$): δ (ppm) 3.68 (s, 2H), 2.22-2.16 (m, 1H), 2.05-1.95 (m, 2H), 1.85-1.64 (m, 3H), 1.40-1.11 (m, 7H), 0.89-0.84 (t, J=7.2 Hz, 3H).

$^{13}$C-RMN (75 MHz, CDCl$_3$): δ (ppm) 172.38, 91.65, 39.58, 38.24, 32.24, 29.50, 20.00, 14.27.

MS [e/m (%)]: 214 (M+, 9), 141 (100), 81 (39), 67(19), 55(22), 41 (15).

IR (pure, cm$^{-1}$): 2926m, 1768s, 1443w, 1223m, 1193m, 1137w, 1043m, 969m, 912w, 842w, 796w, 589w.

EXAMPLE 6

Preparation of 3-methyl-8-propyl-1-oxa-4-thiaspiro[4.5]decan-2-one 3-methyl-8-propyl-1-oxa-4-thiaspiro[4.5]decan-2-one is prepared according to the protocol described in example 1 by using 4-propylcyclohexanone instead of 3,3-dimethylcyclohexanone, thiolactic acid (1.3 equivalents) instead of thioglycolic acid and toluene instead of cyclohexane. The raw product, obtained in the form of two diastereoisomers in proportions 44:56, is distilled under reduced pressure: its boiling point is 95° C. under 0.4 mbar.

Olfactive Description: Peach, Fruity, Green.

3-methyl-8-propyl-1-oxa-4-thiaspiro[4.5]decan-2-one thus obtained has the following spectral features:

Major Isomer (56%):

$^1$H-RMN (300 MHz, CDCl$_3$): δ (ppm) 3.98 (q, J=7.0 Hz, 1H), 2.26-1.61 (m, 6H), 1.56 (d, J=7.0 Hz, 3H), 1.51-0.95 (m, 7H), 0.87 (t, J=7.0 Hz, 3H).

$^{13}$C-RMN (75 MHz, CDCl$_3$): δ (ppm) 175.12, 91.56, 41.39, 40.86, 39.60, 38.95, 38.25, 35.48, 30.12, 20.11, 18.38, 14.26.

SM [EI$^+$] (m/z) (%): 228 [M$^+$] (3), 142 (10), 141 (100), 81 (20), 67 (10)

Minor Isomer (44%):

$^1$H-RMN (300 MHz, CDCl$_3$): δ (ppm) 4.06 (q, J=7.0 Hz, 1H), 2.26-1.61 (m, 6H), 1.57 (d, J=7.0 Hz, 3H), 1.51-0.95 (m, 7H), 0.86 (t, J=7.0 Hz, 3H).

$^{13}$C-RMN (75 MHz, CDCl$_3$): δ (ppm) 175.18, 88.68, 41.39, 40.24, 39.73, 38.30, 35.22, 29.56, 29.40, 19.99, 18.52, 14.26.

SM [EI$^+$] (m/z) (%): 228 [M$^+$] (3), 142 (10), 141 (100), 81 (20), 67 (10), 60 (13)

IR (film, cm$^{-1}$): 1036m, 1224m, 1443m, 1755s, 1926m.

EXAMPLE 7

Preparation of oxathiolanone of spiro[4.5]decan-8-one

Oxathiolanone of spiro[4.5]decan-8-one is prepared according to the protocol described in example 1 by using spiro[4.5]decan-8-one instead of 3,3-dimethylcyclohexanone. The raw product is recrystallised in cyclohexane.

Olfactive Description: Peach, Velvety, Green, Vanilla Effect.

Oxathiolanone of spiro[4.5]decan-8-one thus obtained presents the following spectral features:

$^1$H-RMN (300 MHz, CDCl$_3$): (ppm) 3.74 (s, 2H), 2.16-2.07 (m, 2H), 1.97-1.88 (m, 2H), 1.69-1.59 (m, 6H), 1.54-1.43 (m, 6H).

$^{13}$C-RMN (75 MHz, CDCl$_3$): δ (ppm) 172.42, 93.38, 41.20, 37.02, 34.68, 32.00, 24.45, 24.39.

SM [EI$^+$] (m/z) (%): 226 (M+, 6), 154 (11), 153 (100), 135 (10), 67 (14), 55 (15).

IR (pure, cm$^{-1}$): 2943m, 1771s, 1443m, 1267m, 1221s, 1209s, 1131m, 1041s, 978m, 933m, 900w, 838m, 794m, 608w.

EXAMPLE 8

Preparation of 7,7,9-trimethyl-1-oxa-4-thiaspiro[4.5]decan-2-one 7,7,9-trimethyl-1-oxa-4-thiaspiro[4.5]decan-2-one is prepared according to the protocol described in example 1 by using 3,5,5-trimethylcyclohexanone instead of 3,3-dimethylcyclohexanone. The raw product, obtained in the form of two diastereoisomers in proportions 74:26, is distilled under reduced pressure: its boiling point is 87° C. under 0.04 torr.

Olfactive Description: Peach, Woody, Camphor, Green.

7,7,9-trimethyl-1-oxa-4-thiaspiro[4.5]decan-2-one thus obtained presents the following spectral features:

Major Isomer (74%):

$^1$H-RMN (300 MHz, CDCl$_3$): δ (ppm) 3.73 (s, 2H), 2.19-2.06 (m, 1H), 2.04-1.84 (m, 2H), 1.57-1.25 (m, 3H), 1.06 (s, 3H), 0.97-0.80 (m, 7H).

$^{13}$C-RMN (75 MHz, CDCl$_3$): δ (ppm) 172.53, 91.83, 51.48, 48.37, 46.93, 33.48, 32.74, 32.18, 26.67, 25.98, 21.89.

SM [EI$^+$] (m/z) (%): 214 (M+, 7), 142 (10), 141 (100), 123 (14), 83 (85), 69 (15), 55 (25), 46 (10), 43 (11), 41 (22).

Minor Isomer (26%):

$^1$H-RMN (300 MHz, CDCl$_3$): δ (ppm) 3.65 (s, 2H), 2.19-2.06 (m, 1H), 2.04-1.84 (m, 2H), 1.57-1.25 (m, 3H), 1.04 (s, 3H), 0.97-0.80 (m, 7H).

$^{13}$C-RMN (75 MHz, CDCl$_3$): δ (ppm) 171.99, 93.57, 49.67, 47.62, 47.15, 33.56, 32.46, 32.29, 26.59, 26.38, 21.64.

SM [EI$^+$] (m/z) (%): 214 (M+, 5), 142 (11), 141 (100), 123 (16), 83 (88), 69 (16), 55 (25), 46 (10), 43 (13), 41 (24), 39 (10).

IR (pure, cm$^{-1}$): 2951m, 1766s, 1456w, 1210m, 1167m, 1139w, 1022m, 1005m, 958m, 896w, 859w, 798w, 612w.

EXAMPLE 9

Preparation of 8-pentyl-1-oxa-4-thiaspiro[4.5]decan-2-one 8-pentyl-1-oxa-4-thiaspiro[4.5]decan-2-one is prepared according to the protocol described in example 1 by using 4-pentylcyclohexanone instead of 3,3-dimethylcyclohexanone. The raw product, obtained in the form of two diastereoisomers in proportions 45:55, is distilled under reduced pressure: its boiling point is 135° C. under 0.2 torr.

Olfactive Description: Peach, Fruity, Herbaceous.

8-pentyl-1-oxa-4-thiaspiro[4.5]decan-2-one thus obtained has the following spectral features:

Major Isomer (55%):

$^1$H-RMN (300 MHz, CDCl$_3$): δ (ppm) 3.67 (s, 2H), 2.21-2.14 (m, 1H), 2.06-1.90 (m, 2H), 1.84-1.64 (m, 3H), 1.40-1.11 (m, 11H), 0.88-0.83 (t, J=7.2 Hz, 3H).

$^{13}$C-RMN (75 MHz, CDCl$_3$): δ (ppm) 172.32, 94.45, 38.79, 35.94, 35.76, 32.02, 31.99, 29.76, 22.60, 14.06.

SM [EI$^+$] (m/z) (%): 242 (M+, 4), 170 (12), 169 (100), 95 (24), 81 (24), 67 (12), 55 (24), 43 (12), 41 (23).

Minor Isomer (45%):

$^1$H-RMN (300 MHz, CDCl$_3$): δ (ppm) 3.73 (s, 2H), 2.21-2.14 (m, 1H), 2.06-1.90 (m, 2H), 1.84-1.64 (m, 3H), 1.40-1.11 (m, 11H), 0.88-0.83 (t, J=7.2 Hz, 3H).

$^{13}$C-RMN (75 MHz, CDCl$_3$): δ (ppm) 172.32, 91.61, 39.58, 35.97, 35.49, 32.31, 31.75, 29.53, 26.58, 22.62, 14.27.

SM [e/m (%)]: 242 (M+, 4), 170 (12), 169 (100), 95 (21), 81 (21), 67 (12), 55 (25), 43 (13), 41 (23).

IR (pure, cm$^{-1}$): 2922m, 2853m, 1769s, 1443w, 1209m, 1184m, 1133w, 1041m, 982m, 901w, 796w.

EXAMPLE 10

Perfumed Composition Comprising the Derivatives Obtained in Examples 2, 5 or 7 Applied in a Shampoo Base (at a Rate of 0.6%)

In a rose match produced in the following table (Match A) are added:

8-propyl-1-oxa-4-thiaspiro[4.5]decan-2-one (compound 16025-37, Example 5, Match B)
8-ethyl-1-oxa-4-thiaspiro[4.5]decan-2-one (compound 16025-43, Example 2, Match C)
oxathiolanone of spiro[4.5]decan-8-one (compound 16025-56, Example 7, Match D)

| Ingredients | A | B | C | D |
|---|---|---|---|---|
| CITRONELLOL | 300 | 300 | 300 | 300 |
| GERANIOL | 150 | 150 | 150 | 150 |
| PHENYLETHYL ALCOHOL | 150 | 150 | 150 | 150 |
| PHENOXYETHYL ISOBUTYRATE | 80 | 80 | 80 | 80 |
| DIPHENYL OXIDE | 80 | 80 | 80 | 80 |
| NEROL | 75 | 75 | 75 | 75 |
| ISOAMYL ACETATE 10% DPG | 25 | 25 | 25 | 25 |
| GERANIUM ESS | 20 | 20 | 20 | 20 |
| ROSE OXIDE | 20 | 20 | 20 | 20 |
| CITRAL | 15 | 15 | 15 | 15 |
| OXACYCLOHEXADECAN-2-ONE | 15 | 15 | 15 | 15 |
| MAGNOLAN ™ | 7 | 7 | 7 | 7 |
| DAMASCENONE 10% DPG | 7 | 7 | 7 | 7 |
| FRUCTONE ™ | 5 | 5 | 5 | 5 |
| RASPBERRY KETONE | 5 | 5 | 5 | 5 |
| METHYL PHENYLETHYL ETHER 10% DPG | 5 | 5 | 5 | 5 |
| OXANE 50% TEC | 3 | 3 | 3 | 3 |
| DIMETHYL SULPHIDE | 3 | 3 | 3 | 3 |
| VANILLINE | 1 | 1 | 1 | 1 |
| DIPROPYLENE GLYCOL - DPG | 34 | 29 | 29 | 29 |
| Compound 16025-37 | — | 5 | — | — |
| Compound 16025-43 | — | — | 5 | — |
| Compound 16025-56 | — | — | — | 5 |
| | 1000 | 1000 | 1000 | 1000 |

Adding 5 parts of the compound 16025-37 to the match A boosts the fruity-rose effect of the match elegantly, giving more petal, natural effect, while adding the compound 16025-43 in the same proportions gives a more woody and peach effect, giving a richer and opulent rose. Adding the compound 16026-56 gives a "harder" aspect, through the green. The match is less rosy than in the two preceding cases, fruitier, grapefruit, and still with more power than in the match A.

In both cases, adding a molecule according to the invention gives power and a green note which blends well with the general match of the perfumed composition.

EXAMPLE 11

Perfumed Composition Comprising the Derivatives Obtained in Examples 2, 5 or 7 Applied in a Laundry Softener Base (at a Rate of 1%)

In a fruity-gourmet match produced according to the following table (Match A) are added:
- 8-propyl-1-oxa-4-thiaspiro[4.5]decan-2-one (compound 16025-37, Example 5, Match B)
- 8-ethyl-1-oxa-4-thiaspiro[4.5]decan-2-one (compound 16025-43, Example 2, Match C)
- xathiolanone of spiro[4.5]decan-8-one (compound 16025-56, Example 7, Match D)

| Ingredients | A | B | C | D |
|---|---|---|---|---|
| HEXYLCINNAMIC ALDEHYDE | 125 | 125 | 125 | 125 |
| METHYL DIHYDRO JASMONATE | 80 | 80 | 80 | 80 |
| ETHYL VANILLINE | 75 | 75 | 75 | 75 |
| ISO E | 45 | 45 | 45 | 45 |
| HEXYL SALICYLATE | 45 | 45 | 45 | 45 |
| 4 tBu CYCLOHEXYL ACETATE | 40 | 40 | 40 | 40 |
| HABANOLIDE | 40 | 40 | 40 | 40 |
| VANILLINE | 38 | 38 | 38 | 38 |
| VERDYL ACETATE | 35 | 35 | 35 | 35 |
| 2 tBu CYCLOHEXYL ACETATE 50% DPG | 30 | 30 | 30 | 30 |
| ROSAFIX | 25 | 25 | 25 | 25 |
| TETRAHYDROLINALOL | 25 | 25 | 25 | 25 |
| ANISIC ALDEHYDE | 25 | 25 | 25 | 25 |
| FLOROL ™ | 25 | 25 | 25 | 25 |
| PHENOXYETHYL ISOBUTYRATE | 25 | 25 | 25 | 25 |
| ORANGE TERPENES | 25 | 25 | 25 | 25 |
| GERANIOL | 23 | 23 | 23 | 23 |
| GAMMA UNDECALACTONE | 23 | 23 | 23 | 23 |
| PHENYLETHYL ALCOHOL | 18 | 18 | 18 | 18 |
| ETHYL METHYL PHENYL GLYCIDATE | 17 | 17 | 17 | 17 |
| GAMMA NONALACTONE | 17 | 17 | 17 | 17 |
| ETHYL MALTOL | 14 | 14 | 14 | 14 |
| SILVIAL ™ 10% DPG | 14 | 14 | 14 | 14 |
| ALPHA ISOMETHYL IONONE | 12 | 12 | 12 | 12 |
| GERANYLE ACETATE 10% DPG | 12 | 12 | 12 | 12 |
| LINALYLE ACETATE | 10 | 10 | 10 | 10 |
| 1-(2,3-DIMETHYL-BICYCLO[2.2.1]HEPT-2-YL)-ETHANONE 1% DPG | 9 | 9 | 9 | 9 |
| COUMARINE | 7 | 7 | 7 | 7 |
| CIS-3-HEXENYL SALICYLATE | 7 | 7 | 7 | 7 |
| BENZYL ACETATE | 6 | 6 | 6 | 6 |
| METHYL ANTHRANILATE | 6 | 6 | 6 | 6 |
| FRAMBINONE | 6 | 6 | 6 | 6 |
| DMBC BUTYRATE | 6 | 6 | 6 | 6 |
| ETHYL CINNAMATE | 6 | 6 | 6 | 6 |
| MADERAL ™ | 5 | 5 | 5 | 5 |
| DAMASCENONE 10% DPG | 5 | 5 | 5 | 5 |
| LIFFAROME ™ 10% DPG | 5 | 5 | 5 | 5 |
| ETHYL METHYLVALERATE 10% DPG | 4 | 4 | 4 | 4 |
| DELTA DAMASCONE | 4 | 4 | 4 | 4 |
| HELIOTROPINE | 4 | 4 | 4 | 4 |
| CYCLOGALBANATE ™ 10% DPG | 4 | 4 | 4 | 4 |
| PATCHOULY EO | 2 | 2 | 2 | 2 |
| 6-[2,4,4-TRIMETHYL-CYCLOPENTYLIDENE]-HEXANAL 1% DPG | 2 | 2 | 2 | 2 |
| ORCANOX ™ | 2 | 2 | 2 | 2 |
| Compound 16025-37 | — | 3 | — | — |
| Compound 16025-43 | — | — | 3 | — |
| Compound 16025-56 | — | — | — | 3 |
| DIPROPYLENE GLYCOL - DPG | 50 | 47 | 47 | 47 |
| | 1000 | 1000 | 1000 | 1000 |

Adding 3 parts of the compound 16025-37 to the match A, brings a lot of power and gives a greener, fusing note, while adding the compound 16025-43 rounds the note even more, with a more present and powerful gourmet, vanilla effect.

Adding the compound 16025-56 also rounds the match, while tamping down the fruity notes to this dosage.

EXAMPLE 12

Aromatic Composition Comprising the Derivative Obtained in Example 5 Applied in a Yogurt (at a Rate of 0.08%, that is 160 ppb)

| Ingredients | A | B |
|---|---|---|
| ACETYL METHYL CARBINOL 50% PG | 2 | 2 |
| STRAWBERRY FURANONE 30% PG | 3 | 3 |
| PROPIONIC ACID | 12.5 | 12.5 |
| BUTYRIC ACID | 15 | 15 |
| BUTYLIC ALCOHOL | 15.5 | 15.5 |
| GAMMA DECALACTONE | 17.5 | 17.5 |
| C02 ACETIC ACID | 20 | 20 |
| ETHYL ACETATE | 20 | 20 |
| LINALOL | 25 | 25 |
| C05 METHYL 2 BUTYRIC ACID | 25 | 25 |
| APRICOT B.P.L. | 48.5 | 48.5 |
| GLYCOL PROPYLENE | 796 | 794.5 |
| Compound 16025-37 10% PG | — | 2 |
| | 1000 | 1000 |

Adding the compound 16025-37 to 160 ppb in the yogurt gives the peach flavour a more authentic, rounder, peach nectar profile.

EXAMPLE 13

Aromatic Composition Comprising the Derivative Obtained in Example 5 Applied in a Yogurt (at a Rate of 0.02%, that is 140 ppb)

| Ingredients | A | B |
|---|---|---|
| BUTYRIC ACID | 15 | 15 |
| GAMMA DECALACTONE | 7 | 7 |
| C02 ACETIC ACID | 12 | 12 |
| LINALOL | 1.5 | 1.5 |
| C05 BUTYRIC METHYL 2 ACID | 6 | 6 |
| THIAZOLE ISOPROPYL METHYL 1% ALC | 1 | 1 |
| BUCHU ESSENCE DETERPENE 1% ALC | 1.4 | 1.4 |
| GERANYLE ACETATE | 1.5 | 1.5 |
| GAMMA HEXALACTONE S | 2.5 | 2.5 |
| HEXYL ACETATE | 3 | 3 |
| BENZOIC ALDEHYDE | 3 | 3 |
| DELTA DECALACTONE | 3 | 3 |
| MALTOL | 3 | 3 |
| GAMMA DODECALACTONE S | 3.5 | 3.5 |
| HEXENOL CIS 3 | 4.5 | 4.5 |

-continued

| Ingredients | A | B |
|---|---|---|
| HEXENYL CIS 3 ACETATE | 9 | 9 |
| LIMONENE | 9 | 9 |
| ISOAMYLE ACETATE | 15 | 15 |
| C02 ETHYLIC ALCOHOL | 899.1 | 897.1 |
| Compound 16025-37 10% PG |  | 7 |
|  | 1000 | 1000 |

Adding the compound 16025-37 at a rate of 140 ppb complexifies the apricot profile, brings a very natural side, apricot flesh, juice, very tasty. The profile of this apricot flavour is very particular and has not been able to be reproduced using other compounds of the prior art.

EXAMPLE 14

Olfactometry Tests

It is generally admitted that the ratio of the volatility by the detection threshold of an odour makes it possible to obtain an "odour value" with no unit, considering the olfactive power of a molecule. The greater this value is, the more powerful the molecule in question is. In order to calculate this odour value, the volatility, as well as the detection threshold must consequently be determined.

In the present study, two molecules of the invention are tested in order to determine their power (via their odour value) with respect to a reference molecule of the prior art, gamma-undecalactone. The two molecules according to the invention which are tested are that of example 2 (8-ethyl-1-oxa-4-thiaspiro[4.5]decan-2-one) and that of example 5 (8-propyl-1-oxa-4-thiaspiro[4.5]decan-2-one).

Initially, the volatility values at 20° C. of the molecules of example 2 and example 5 are determined by ebulliometry. These values are respectively 19.8 µg·l$^{-1}$ and 7.8 µg·l$^{-1}$.

Secondly, psychosensorial studies have been carried out, in order to determine the detection threshold of the two molecules according to the present invention and as well as that of gamma-undecalactone.

The value of the detection threshold is obtained using a dynamic olfactometer constructed according to the guidelines of the standards ISO 13725 and ISO 13301. It corresponds to the critical statistical gaseous concentration to trigger a positive response for a set of eighteen panellists as a minimum, of which the age varies from 22 to 57 years old according to a model of a forced choice from among two. One of these choices is the controlled dilution of an airflow saturated in raw material, the other choice is a neutral airflow. The random repetition of these choices for a set of five to eight gaseous concentrations, thus allows the determination of the detection threshold after statistical treatment of the data obtained. Thus, the detection threshold for the molecules of example 2 and example 5 have been determined and are respectively 0.016 ng·l$^{-1}$ and 0.075 ng·l$^{-1}$.

Thus, after these measurements, it is possible to calculate the odour value of the molecules according to the invention in comparison with that of gamma-undecalactone.

Odour Value=Volatility value/Detection threshold

The Odour Value is equal to 1222223 for the molecule according to example 2, and to 104133 for the molecule according to example 5. Yet, for gamma-undecalactone, the Odour Value determined under identical experimental conditions is 5473.

In conclusion, the Odour Value of the molecules according to the invention (of examples 2 and 5) is very clearly greater than that of gamma-undecalactone which indicates said molecules according to the invention are very clearly more powerful than gamma-undecalactone.

Furthermore, the substantivity evaluated by the panellists is equal to 2.59 for the molecule according to example 2, and to 2.62 for the molecule according to example 5.

The invention claimed is:

1. A compound of the following general formula (I):

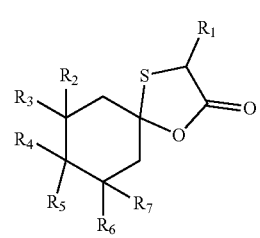

wherein:
R$_1$, R$_2$, R$_3$, R$_4$, R$_6$ and R$_7$, represent independently a hydrogen atom or a methyl group;
R$_5$ represents a hydrogen atom or a saturated linear C$_1$-C$_5$ alkyl group;
R$_4$ and R$_5$ could together form a cyclopentyl group; and
the total number of carbon atoms is greater than 9,
with the proviso that when R$_1$, R$_2$, R$_3$, R$_4$, and R$_7$ are all hydrogen, R$_5$ is not t-butyl, wherein the compound has aromatic or olfactive properties.

2. The compound according to claim 1, wherein R$_5$ represents a saturated linear C$_1$-C$_5$ alkyl group.

3. The compound according to claim 1, wherein R$_1$, R$_2$, R$_3$, R$_4$, R$_6$ and R$_7$, represent a hydrogen atom.

4. The compound according to claim 1, wherein the total number of carbon atoms is 10 or 11.

5. The compound according to claim 1, wherein the compound is selected from the group consisting of 7,7-dimethyl-1-oxa-4-thiaspiro[4.5]decan-2-one, 8-ethyl-1-oxa-4-thiaspiro[4.5]decan-2-one, 8-ethyl-3-methyl-1-oxa-4-thiaspiro[4.5]decan-2-one, 8,8-dimethyl-1-oxa-4-thiaspiro[4.5]decan-2-one, 8-propyl-1-oxa-4-thiaspiro[4.5]decan-2-one, 3-methyl-8-propyl-1-oxa-4-thiaspiro[4.5]decan-2-one, oxathiolanone of spiro[4.5]decan-8-one, 7,7,9-trimethyl-1-oxa-4-thiaspiro[4.5]decan-2-one and 8-pentyl-1-oxa-4-thiaspiro[4.5]decan-2-one.

6. A method for preparing a compound of formula (I) according to claim 1 comprising performing a cyclisation reaction between a cycloalcanone of formula (II) and a thiol acid of formula (III) in the presence of an acid as follows:

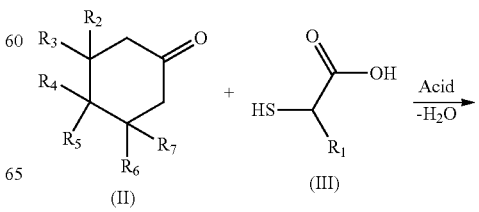

-continued

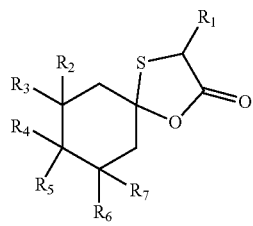

wherein:

R$_1$, R$_2$, R$_3$, R$_4$, R$_6$ and R$_7$, represent independently a hydrogen atom or a methyl group;

R$_5$ represents a hydrogen atom or a saturated linear C$_1$-C$_5$ alkyl group;

R$_4$ and R$_5$ could together form a cyclopentyl group; and the total number of carbon atoms is greater than 9.

7. The method according to claim 6, wherein the thiol acid is thioglycolic acid.

8. The method according to claim 6, wherein the thiol acid is thiolactic acid.

9. The method according to claim 6, wherein the cyclization reactions is performed in the present of a sulphonic para-toluene acid.

10. A method of providing, modifying, or reinforcing the organoleptic properties of a substance, a composition, or an article comprising using at least one compound of general formula (I) according to claim 1 in the form of a stereoisomer, a mixture of stereoisomers, or a racemic mixture to provide, modify, or reinforce the organoleptic properties of a substance, a composition or an article.

11. The method according to claim 10 wherein at least one compound of formula (I) is used as a fragrant agent, individually or in combination with another component selected from the group consisting of an odorising substance, a solvent, and an additive.

12. The method according to claim 10 wherein at least one compound of general formula (I) is used as an aromatic compound, individually or in combination with another component selected from the group consisting of an aromatic substance, a solvent, and an additive.

13. A composition comprising a compound of the following general formula (I):

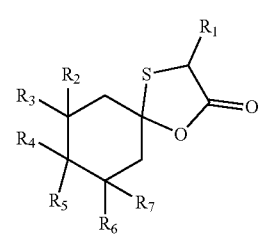

wherein:

R$_1$, R$_2$, R$_3$, R$_4$, R$_6$ and R$_7$, represent independently a hydrogen atom or a methyl group;

R$_5$ represents a hydrogen atom or a saturated linear C$_1$-C$_5$ alkyl group;

R$_4$ and R$_5$ could together form a cyclopentyl group; and the total number of carbon atoms being strictly greater than 9, with the proviso that when R$_1$, R$_2$, R$_3$, R$_4$, and R$_7$ are all hydrogen, R$_5$ is not t-butyl; and, wherein said composition further comprises an inert support material, wherein the compound has aromatic or olfactive properties.

14. The composition according to claim 13 wherein the compound is selected from the group consisting of 7,7-dimethyl-1-oxa-4-thiaspiro[4.5]decan-2-one, 8-ethyl-1-oxa-4-thiaspiro[4.5]decan-2-one, 8-ethyl-3-methyl-1-oxa-4-thiaspiro[4.5]decan-2-one, 8,8-dimethyl-1-oxa-4-thiaspiro[4.5]decan-2-one, 8-propyl-1-oxa-4-thiaspiro[4.5]decan-2-one, 3-methyl-8-propyl-1-oxa-4-thiaspiro[4.5]decan-2-one, oxathiolanone of spiro[4.5]decan-8-one, 7,7,9-trimethyl-1-oxa-4-thiaspiro[4.5]decan-2-one and 8-pentyl-1-oxa-4-thiaspiro[4.5]decan-2-one.

15. The composition according to claim 13, wherein the compound of formula (I) is present in a concentration comprising between 0.000001 to 50% by weight with respect to the total weight of the composition.

16. The composition according to claim 13, wherein said composition is a perfume comprising at least one compound of formula (I) and at least one odorising substance.

17. The composition according to claim 13, wherein said composition is an aromatic composition comprising at least one compound of formula (I) and at least one aromatic substance.

18. The composition according to claim 13, wherein the compound of formula (I) is present in a concentration comprising between 0.000005 to 20% weight with respect to the total weight of the composition.

* * * * *